US 8,685,330 B2

(12) United States Patent
Irvin et al.

(10) Patent No.: US 8,685,330 B2
(45) Date of Patent: *Apr. 1, 2014

(54) AIR FRESHENER FLOWER WITH VENT STICK

(75) Inventors: Aaron Irvin, Salt Lake City, UT (US); Alan J. Wheatley, Draper, UT (US); Christopher D. Anderson, Draper, UT (US)

(73) Assignee: American Covers, Inc., Draper, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/359,726

(22) Filed: Jan. 27, 2012

(65) Prior Publication Data

US 2013/0028798 A1  Jan. 31, 2013

Related U.S. Application Data

(63) Continuation-in-part of application No. 12/623,007, filed on Nov. 20, 2009, now Pat. No. 8,147,761, which is a continuation of application No. 12/243,635, filed on Oct. 1, 2008, now Pat. No. 7,687,038, which is a continuation of application No. 11/264,670, filed on Oct. 31, 2005, now Pat. No. 7,687,037, said application No. 12/623,007 is a continuation of application No. 11/264,670, application No. 13/359,726, which is a continuation-in-part of application No. 13/009,574, filed on Jan. 19, 2011, which is a continuation of application No. 12/623,007, which is a continuation of application No. 11/264,670, and a continuation of application No. 12/243,635, which is a continuation-in-part of application No. 11/264,670.

(51) Int. Cl.
*A62B 7/08* (2006.01)
*A61L 9/00* (2006.01)

(52) U.S. Cl.
USPC ............... 422/123; 422/120; 422/122; 422/5

(58) Field of Classification Search
USPC ...................... 422/120, 122, 123, 5
See application file for complete search history.

(56) References Cited

U.S. PATENT DOCUMENTS

| D176,671 S | 4/1876 | Myers |
|---|---|---|
| 369,878 A | 9/1887 | Palmer |

(Continued)

FOREIGN PATENT DOCUMENTS

| CA | 2077251 | 5/1993 |
|---|---|---|
| EP | 0 348 970 | 1/1990 |

(Continued)

OTHER PUBLICATIONS about.com Housekeeping, http://housekeeping.about.com/od/pr...af-fresh, Febrezee Noticeables, accessed Oct. 2, 2008, 2 pages.

(Continued)

*Primary Examiner* — Regina M Yoo
(74) *Attorney, Agent, or Firm* — Thorpe North & Western LLP

(57) ABSTRACT

An air freshener has a vent rod and a scent material carried by the vent rod. A head is pivotally coupled to the vent rod. A hinge is between the head and the vent rod including an axel in an aperture. A plurality of petals is coupled to the head and pivotal with the head with respect to the vent rod.

20 Claims, 7 Drawing Sheets

(56) References Cited

U.S. PATENT DOCUMENTS

| | | |
|---|---|---|
| 1,171,737 A | 2/1916 | Madgan |
| D140,109 S | 1/1945 | Pierce |
| 2,642,248 A | 6/1953 | Semon |
| 2,733,333 A | 1/1956 | Peters |
| D177,826 S | 5/1956 | Katz |
| D178,237 S | 7/1956 | Katz |
| 3,239,145 A | 3/1966 | Aurelio |
| 3,456,106 A | 7/1969 | Gluschkin |
| 3,552,632 A * | 1/1971 | Wilson .......................... 206/0.5 |
| 3,655,129 A | 4/1972 | Seiner |
| 3,847,305 A | 11/1974 | Tobin |
| 3,948,445 A | 4/1976 | Andeweg |
| 3,971,858 A | 7/1976 | Collier et al. |
| D246,986 S | 1/1978 | Costello |
| 4,084,079 A | 4/1978 | Costello |
| D250,041 S | 10/1978 | Schimanski |
| 4,149,675 A | 4/1979 | Van Breen et al. |
| 4,184,099 A | 1/1980 | Lindauer et al. |
| 4,226,944 A | 10/1980 | Stone et al. |
| D258,511 S | 3/1981 | Ashton |
| 4,280,649 A | 7/1981 | Montealegre |
| 4,301,949 A | 11/1981 | Palson et al. |
| 1,683,545 A | 9/1982 | Harris |
| 4,382,548 A | 5/1983 | van der Heijden |
| 4,391,781 A | 7/1983 | van Lit |
| 4,517,326 A | 5/1985 | Cordts et al. |
| 4,549,693 A | 10/1985 | Barlics |
| 4,594,380 A | 6/1986 | Chapin et al. |
| D286,323 S | 10/1986 | Haworth |
| 4,638,057 A | 1/1987 | Takahashi et al. |
| 4,649,046 A | 3/1987 | Kross |
| 4,703,070 A | 10/1987 | Locko et al. |
| RE32,834 E | 1/1989 | Cordts et al. |
| 4,808,347 A | 2/1989 | Dawn |
| 4,840,773 A | 6/1989 | Wade |
| 4,849,606 A | 7/1989 | Martens et al. |
| 4,874,129 A | 10/1989 | DiSapio et al. |
| 4,880,690 A | 11/1989 | Szycher et al. |
| 4,950,542 A | 8/1990 | Barker |
| 4,968,456 A | 11/1990 | Muderlak et al. |
| 5,008,115 A | 4/1991 | Lee et al. |
| 5,019,434 A | 5/1991 | Matsumoto |
| 5,034,222 A | 7/1991 | Kellett et al. |
| D319,781 S | 9/1991 | Halm et al. |
| 5,050,798 A | 9/1991 | Sullivan |
| D322,558 S | 12/1991 | Halm et al. |
| 5,071,704 A | 12/1991 | Fischel-Ghodsian |
| 5,114,625 A | 5/1992 | Gibson |
| 5,120,583 A | 6/1992 | Garcia |
| 5,178,327 A | 1/1993 | Palamand et al. |
| 5,180,107 A | 1/1993 | Lindauer |
| 5,193,445 A | 3/1993 | Ferguson |
| D334,975 S | 4/1993 | Bunce |
| 5,220,636 A | 6/1993 | Chang |
| D338,519 S | 8/1993 | Peterson |
| 5,234,162 A | 8/1993 | Sullivan |
| 5,240,487 A | 8/1993 | Kung |
| D349,157 S | 7/1994 | Rymer |
| D350,192 S | 8/1994 | Patel et al. |
| 5,368,822 A | 11/1994 | McNeil |
| 5,407,642 A | 4/1995 | Lord |
| 5,422,078 A | 6/1995 | Colon |
| D367,526 S | 2/1996 | Bignon |
| D367,924 S | 3/1996 | Patel et al. |
| 5,520,921 A | 5/1996 | Chalifoux |
| D373,626 S | 9/1996 | Dente et al. |
| D375,350 S | 11/1996 | Patel et al. |
| 5,595,194 A | 1/1997 | Talbot |
| D380,258 S | 6/1997 | Muller et al. |
| 5,651,522 A | 7/1997 | Davis et al. |
| 5,683,285 A | 11/1997 | Wong |
| 5,695,692 A | 12/1997 | Kennedy |
| 5,704,832 A | 1/1998 | Borrell |
| D390,941 S | 2/1998 | Cessaroni et al. |
| D392,032 S | 3/1998 | Zaragoza et al. |
| 5,725,152 A * | 3/1998 | Akyu .............................. 239/45 |
| 5,762,549 A | 6/1998 | Scheuer et al. |
| 5,780,527 A | 7/1998 | O'Leary |
| 2,794,767 A | 8/1998 | Wilson |
| 5,820,791 A | 10/1998 | Canale |
| D400,662 S | 11/1998 | Davis |
| 5,845,847 A | 12/1998 | Martin et al. |
| 5,860,552 A | 1/1999 | Culhane et al. |
| 5,861,128 A | 1/1999 | Vick et al. |
| D404,957 S | 2/1999 | Cheris et al. |
| 5,871,765 A | 2/1999 | Johnson et al. |
| 5,899,382 A | 5/1999 | Hayes |
| D410,540 S | 6/1999 | Pinchuk |
| D411,002 S | 6/1999 | Farmer |
| D415,267 S | 10/1999 | Kauzlarich et al. |
| D415,268 S | 10/1999 | Farmer |
| 5,988,520 A | 11/1999 | Bitner |
| D417,727 S | 12/1999 | Christianson |
| 6,044,202 A | 3/2000 | Junkel |
| D424,677 S | 5/2000 | Chen |
| D425,190 S | 5/2000 | Morikawa |
| 6,111,055 A | 8/2000 | Berger et al. |
| 6,123,906 A | 9/2000 | Farmer |
| 6,123,935 A | 9/2000 | Wefler et al. |
| D432,222 S | 10/2000 | Rymer et al. |
| D435,694 S | 12/2000 | Lebherz |
| D437,038 S | 1/2001 | Chuan |
| D437,041 S | 1/2001 | Eisenbraun |
| 6,190,607 B1 | 2/2001 | Farmer |
| 6,191,197 B1 | 2/2001 | Wang et al. |
| 6,197,263 B1 | 3/2001 | Blount |
| 6,202,938 B1 | 3/2001 | Collier |
| D440,294 S | 4/2001 | Bilek |
| D441,441 S | 5/2001 | Upson |
| 6,264,887 B1 | 7/2001 | Farmer |
| 6,291,371 B1 | 9/2001 | Shefer et al. |
| 6,309,715 B1 | 10/2001 | Lindauer et al. |
| 6,325,475 B1 | 12/2001 | Hayes et al. |
| D454,190 S | 3/2002 | Trocola |
| 6,357,260 B1 | 3/2002 | Lutz |
| 6,374,044 B1 | 4/2002 | Freidel |
| 6,375,966 B1 | 4/2002 | Maleeny et al. |
| 6,379,689 B1 | 4/2002 | Aguadisch |
| 6,391,398 B1 * | 5/2002 | Pesu et al. ........................ 428/13 |
| 6,416,043 B1 | 7/2002 | Eisenbraun |
| 6,514,467 B1 | 2/2003 | Bulsink et al. |
| D472,968 S | 4/2003 | Christianson |
| D478,379 S | 8/2003 | Talenton et al. |
| D478,973 S | 8/2003 | Wagner |
| D479,592 S | 9/2003 | Lammel et al. |
| D485,343 S | 1/2004 | Wu |
| D487,504 S | 3/2004 | Yuen |
| 6,712,286 B2 | 3/2004 | Baxter et al. |
| D488,214 S | 4/2004 | Quantin |
| D488,548 S | 4/2004 | Lablaine |
| D491,257 S | 6/2004 | Picken |
| D491,798 S | 6/2004 | Buthier |
| D496,720 S | 9/2004 | Dudley |
| 6,800,252 B1 | 10/2004 | Jedzinski |
| 6,830,733 B2 * | 12/2004 | Stanley, III .................... 422/124 |
| 6,885,811 B2 | 4/2005 | He et al. |
| D504,943 S | 5/2005 | Dudley |
| D507,341 S | 7/2005 | Taylor |
| D511,568 S | 11/2005 | Wheatley |
| D514,679 S | 2/2006 | Wheatley |
| D515,192 S | 2/2006 | Smith et al. |
| 7,025,283 B2 | 4/2006 | Torres |
| 7,055,764 B1 | 6/2006 | Martinez et al. |
| 7,061,386 B2 | 6/2006 | Seresini |
| 7,137,570 B2 | 11/2006 | Wheatley et al. |
| D535,376 S | 1/2007 | Michaels et al. |
| D535,379 S | 1/2007 | Hundertmark |
| 7,159,792 B2 | 1/2007 | Wheatley et al. |
| D544,080 S | 6/2007 | Carlson |
| D544,084 S | 6/2007 | Michaels et al. |
| D544,594 S | 6/2007 | Zobele |
| D544,953 S | 6/2007 | Kee |
| D546,432 S | 7/2007 | Hundertmark |
| 7,243,859 B2 | 7/2007 | Caserta et al. |

(56) References Cited

U.S. PATENT DOCUMENTS

| | | | |
|---|---|---|---|
| D548,317 S | 8/2007 | Newton et al. |
| D550,345 S | 9/2007 | Weggelaar |
| D551,333 S | 9/2007 | Wu |
| 7,285,248 B2 | 10/2007 | Yamamoto et al. |
| D554,746 S | 11/2007 | Davis et al. |
| 7,293,719 B2 | 11/2007 | Wheatley |
| D565,162 S | 3/2008 | Carlson |
| 7,344,123 B2 | 3/2008 | Pankhurst et al. |
| D565,715 S | 4/2008 | Wu |
| D573,706 S | 7/2008 | Zlotnik et al. |
| D574,941 S | 8/2008 | Weggelaar |
| 7,441,360 B2 | 10/2008 | Christianson et al. |
| D580,039 S | 11/2008 | Zlotnik et al. |
| D585,129 S | 1/2009 | Huang |
| D585,971 S | 2/2009 | Carrizales |
| D591,415 S | 4/2009 | Wu |
| D593,670 S | 6/2009 | Valentino et al. |
| D594,953 S | 6/2009 | King et al. |
| D594,954 S | 6/2009 | Wheatley |
| 7,544,332 B2 | 6/2009 | De Silva et al. |
| D597,645 S | 8/2009 | Thompson |
| D598,531 S | 8/2009 | Irvin |
| D604,825 S | 11/2009 | Brandenburg |
| D607,983 S | 1/2010 | Irvin |
| 7,651,666 B2 | 1/2010 | Adair et al. |
| 7,670,566 B2 | 3/2010 | Adair et al. |
| 7,687,037 B2 | 3/2010 | Wheatley |
| 7,687,038 B2 | 3/2010 | Wheatley |
| D614,277 S | 4/2010 | Hsiao |
| D619,692 S | 7/2010 | Hami et al. |
| D619,693 S | 7/2010 | Hami et al. |
| D619,694 S | 7/2010 | Hami et al. |
| D620,573 S | 7/2010 | Hami et al. |
| D622,835 S | 8/2010 | Mendheim |
| 7,780,094 B2 | 8/2010 | Caserta et al. |
| D625,798 S | 10/2010 | Hami et al. |
| D629,881 S | 12/2010 | Valentino et al. |
| D631,534 S | 1/2011 | Kajizuka |
| D631,954 S | 2/2011 | Bertassi et al. |
| D633,610 S | 3/2011 | Wu |
| D637,275 S | 5/2011 | Baraky |
| D640,358 S | 6/2011 | Irvin |
| D640,781 S | 6/2011 | Brandenburg |
| D642,668 S | 8/2011 | Lablaine |
| D645,949 S | 9/2011 | Brandenburg et al. |
| D647,186 S | 10/2011 | Chan et al. |
| D649,237 S | 11/2011 | Bilko et al. |
| D650,892 S | 12/2011 | Wheatley |
| 8,147,761 B2 * | 4/2012 | Wheatley et al. ............. 422/123 |
| D660,950 S | 5/2012 | Finlay |
| D662,581 S | 6/2012 | Savegnago |
| 8,251,299 B1 | 8/2012 | Irvin |
| D667,100 S | 9/2012 | Hakim |
| 8,485,454 B1 | 7/2013 | Irvin |
| 8,490,846 B1 | 7/2013 | Wheatley |
| 2001/0051234 A1* | 12/2001 | Ryan et al. ....................... 428/24 |
| 2003/0097936 A1 | 5/2003 | Maleeny et al. |
| 2003/0199421 A1 | 10/2003 | Copfer |
| 2004/0197221 A1* | 10/2004 | Stanley, III ........................ 422/5 |
| 2004/0265164 A1 | 12/2004 | Woo et al. |
| 2005/0084413 A1* | 4/2005 | Stanley, III ........................ 422/5 |
| 2005/0127538 A1 | 6/2005 | Fabrega et al. |
| 2005/0169793 A1 | 8/2005 | Wheatley et al. |
| 2006/0043216 A1 | 3/2006 | Robinson |
| 2006/0078477 A1 | 4/2006 | Althouse et al. |
| 2006/0196964 A1 | 9/2006 | Wheatley et al. |
| 2006/0279008 A1 | 12/2006 | Jursich |
| 2007/0057084 A1 | 3/2007 | Vieira |
| 2007/0160492 A1 | 7/2007 | Spector |
| 2007/0231508 A1* | 10/2007 | Fand et al. ........................ 428/24 |
| 2007/0290064 A1 | 12/2007 | Majerowski et al. |
| 2008/0099576 A1 | 5/2008 | Hart |
| 2008/0128925 A1 | 6/2008 | Pankhurst et al. |
| 2008/0311315 A1* | 12/2008 | Marlow ........................... 428/24 |
| 2008/0311316 A1* | 12/2008 | Marlow ........................... 428/24 |
| 2009/0008411 A1 | 1/2009 | Schumacher et al. |
| 2009/0010813 A1 | 1/2009 | Wang et al. |
| 2009/0072045 A1 | 3/2009 | Wheatley et al. |
| 2009/0173799 A1 | 7/2009 | Litten-Brown et al. |
| 2010/0010409 A1 | 1/2010 | Bejarano |
| 2010/0019059 A1 | 1/2010 | Bulsink et al. |
| 2010/0065654 A1 | 3/2010 | Wheatley et al. |
| 2010/0187327 A1 | 7/2010 | Irvin |
| 2010/0288847 A1 | 11/2010 | Gruenbacher et al. |
| 2011/0108632 A1 | 5/2011 | Brandenburg et al. |
| 2011/0110823 A1 | 5/2011 | Wheatley et al. |
| 2012/0076276 A1 | 3/2012 | Wang et al. |

FOREIGN PATENT DOCUMENTS

| | | |
|---|---|---|
| EP | 1 346 734 | 9/2003 |
| WO | WO 98/46284 | 10/1998 |
| WO | WO 00/24434 | 5/2000 |
| WO | WO 00/64498 | 11/2000 |
| WO | WO 02/35975 | 5/2002 |
| WO | WO 02/38029 | 5/2002 |
| WO | WO 2004/078219 | 9/2004 |
| WO | WO 2006/010282 | 2/2006 |
| WO | WO 2006/084160 | 8/2006 |
| ZA | 20004637 | 9/2000 |

OTHER PUBLICATIONS

Aromate E-News, Innovation in Novelty Fragrance, Http://209.85.173.104/seasrch?qcach . . . , accessed Oct. 8, 2008, 2 pages.

Ecrater, www.ecrater.com/product.hp?. . . , Yankee Candle Selects Two Scents Electric Fragrance Unit Macintosh/Home Sweet Home, accessed Oct. 2, 2008, 1 page.

http://decomodo.com/articles/categor/lighting/, Bamboo Pillar Candle, Jan. 8, 2008, 1 page.

http://shop.advanceautoparts.com/webapp/wcs/stores/servlet/product_6170795-P_N3004...Advance Auto Part; Arometrics Dual-Scent Vent—Juicy Strawberry and Vanilla; 1 Page; accessed Dec. 10, 2010.

http://www.bestliquidations.com/Medo_Vent Frehser.htm; BestLiquidations.com; Medo Vent Fresh Air Fresheners; 2 pages; accessed Dec. 10, 2010.

Medo® Air Fresheners; Auto Expressions™ 2005 Product Catalog; 25 pages.

Pictures (3) of Medo® auto Expressions Vent™ Air Freshener distributed by SOPUS Products of Moorpark, CA 2003 copyright date on package.

Scents & Sprays, www.scentsandsprays.com/ya . . . , Yankee Autumn Bounty Electric 2 Home Air Fresheners, copyright 2001-2008 scentsandsprays.com, accessed Oct. 2, 2008, 1 page.

www.4imprint.com/EXEC/DETAIL/FROMPRODUCTGROUP/~SKU100300/~CA100300.htm, Hot Rod Vent Stick Air Freshener (it . . . , accessed Aug. 12, 2008, 2 pages.

www.autothing.com/Products/Air%20Fresheners/air%20freshener-clip.htm, Air Fresheners, Fresh Scents for you mobile Life, Clip-on Air Vent Clips rom Eagle o., Accessed Aug. 12, 2008, 1 page.

www.chicscents.com/Products.aspx Island Adventure Sandals; 2 pages; accessed Feb. 1, 2011.

www.chicscents.com/Products.aspx; Inspiration 3-D by Chic; 2 pages; accessed Feb. 1, 2011.

U.S. Appl. No. 12/979,763, filed Dec. 28, 2010; Aaron Irvin.

U.S. Appl. No. 12/979,795, filed Dec. 28, 2010; Aaron Irvin.

U.S. Appl. No. 12/979,813, filed Dec. 28, 2010; Aaron Irvin.

U.S. Appl. No. 13/191,966, filed Jul. 27, 2011; Aaron Irvin.

U.S. Appl. No. 12/979,763, filed Dec. 28, 2010; Aaron Irvin; office action dated Dec. 14, 2012.

U.S. Appl. No. 12/693,543, filed Jan. 26, 2010; Aaron Irvin; office action dated Dec. 18, 2012.

U.S. Appl. No. 13/009,574, filed Jan. 19, 2011; Alan J. Wheatley; office action dated Jan. 11, 2013.

U.S. Appl. No. 12/979,795, filed Dec. 28, 2010; Aaron Irvin; office action dated Jan. 28, 2013.

U.S. Appl. No. 12/979,813, filed Dec. 28, 2010; Aaron Irvin; office action dated Jan. 31, 2013.

U.S. Appl. No. 12/915,983, filed Oct. 29, 2010; Alan J. Wheatley;

(56) References Cited

OTHER PUBLICATIONS notice of allowance dated Feb. 20, 2013.
Ecrater, www.ecrater.com/product.hp? . . . , Yankee Candle Selects Two Scents Electric Fragrance Unit Macintosh/Home Sweet Home, accessed Oct. 2, 2008, 1 page.
U.S. Appl. No. 12/378,121, filed Oct. 29, 2010; Aaron Irvin.
U.S. Appl. No. 12/915,924, filed Oct. 29, 2010; Nathaniel Finlay.
U.S. Appl. No. 12/915,983, filed Oct. 29, 2010; Alan J. Wheatley.
U.S. Appl. No. 12/916,038, filed Oct. 29, 2010; Aaron Irvin.
U.S. Appl. No. 29/378,112, filed Oct. 29, 2010; Nathaniel Finlay.
U.S. Appl. No. 13/281,890, filed Oct. 26, 2011; Aaron Irvin.
U.S. Appl. No. 13/282,035, filed Oct. 26, 2011; Nathaniel Finlay.
U.S. Appl. No. 29/378,112, filed Oct. 29, 2010; Nathaniel Finlay; Notice of Allowance issued Mar. 29, 2012.
U.S. Appl. No. 12/916,038, filed Oct. 29, 2010; Aaron Irvin; Notice of Allowance issued Apr. 27, 2012.
U.S. Appl. No. 29/415,358, filed Mar. 9, 2012; Aaron Irvin; Notice of Allowance issued May 29, 2012.
U.S. Appl. No. 12/979,813, filed Dec. 28, 2010; Aaron Irvin; office action dated Sep. 14, 2012.
U.S. Appl. No. 12/979,795, filed Dec. 28, 2010; Aaron Irvin; office action dated Sep. 13, 2012.
U.S. Appl. No. 12/693,543, filed Jan. 26, 2010; Aaron Irvin; office action dated Aug. 7, 2012.
U.S. Appl. No. 12/979,763, filed Dec. 28, 2010; Aaron Irvin notice of allowance dated Apr. 15, 2013.
U.S. Appl. No. 13/282,035, filed Oct. 26, 2011; Nathaniel Finlay, office action dated Apr. 17, 2013.
U.S. Appl. No. 12/987,662, filed Jan. 10, 2011; Alan J. Wheatley; notice of allowance dated Jun. 7, 2013.
U.S. Appl. No. 12/979,690, filed Dec. 28, 2010; Alan J. Wheatley; notice of allowance dated Jun. 10, 2013.
U.S. Appl. No. 12/979,601, filed Dec. 28, 2010; Alan J. Wheatley; notice of allowance dated Jun. 10, 2013.
U.S. Appl. No. 29/435,391, filed Oct. 23, 2012; Aaron Irvin, notice of allowance dated Jun. 18, 2013.
U.S. Appl. No. 29/435,389, filed Oct. 23, 2012; Aaron Irvin; notice of allowance dated Mar. 1, 2013.
U.S. Appl. No. 13/009,574, filed Jan. 19, 2011; Alan Wheatley; notice of allowance dated Apr. 3, 2013.
U.S. Appl. No. 13/359,726, filed Jan. 27, 2012; Aaron Irvin; office action dated Apr. 5, 2013.
U.S. Appl. No. 12/979,601, filed Dec. 28, 2010; Alan J. Wheatley; office action dated Mar. 1, 2013.
U.S. Appl. No. 13/282,035; filed Oct. 26, 2011; Nathaniel Finlay; office action dated Jul. 17, 2013.

\* cited by examiner

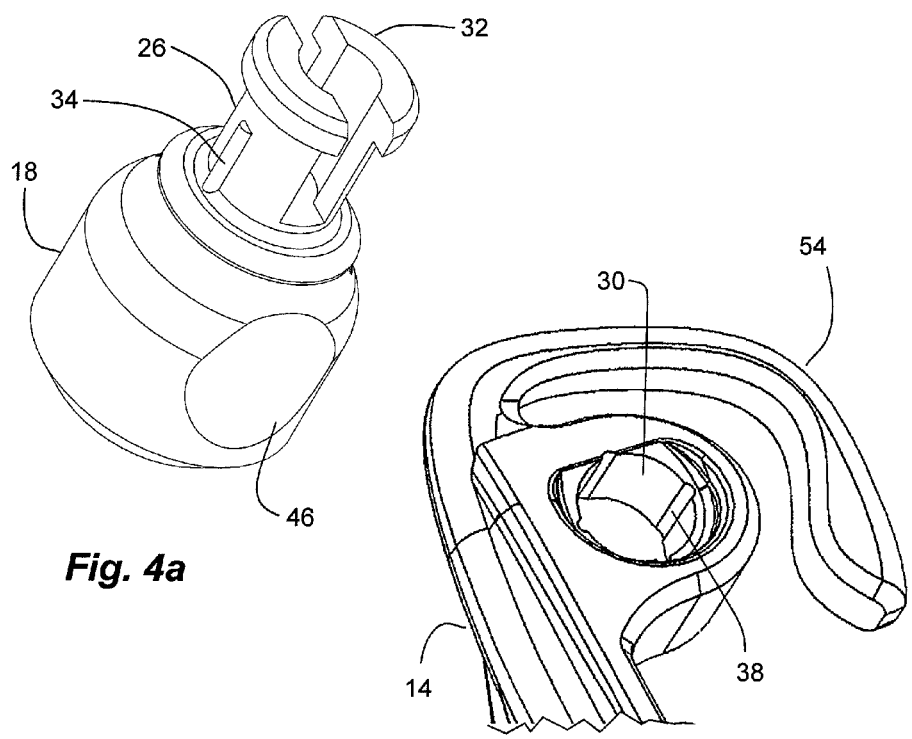
Fig. 4a
Fig. 3f
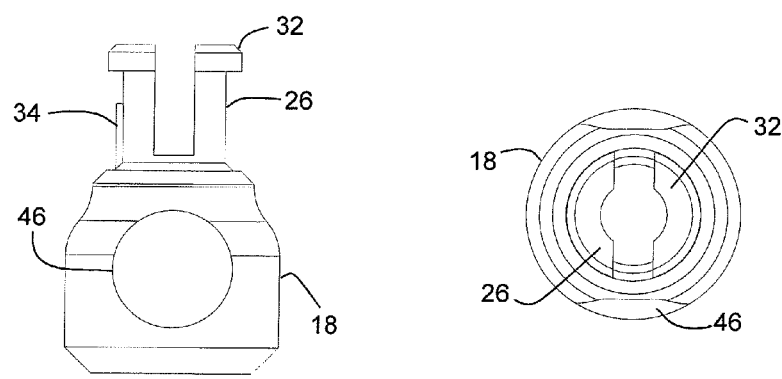
Fig. 4b
Fig. 4c

AIR FRESHENER FLOWER WITH VENT STICK

PRIORITY CLAIM

This is a continuation-in-part of U.S. patent application Ser. No. 12/623,007, filed Nov. 20, 2009; U.S. Pat. No. 8,147,761 which is a continuation of U.S. patent application Ser. No. 12/243,635, filed Oct. 1, 2008, now U.S. Pat. No. 7,687,038; which is a continuation of U.S. patent application Ser. No. 11/264,670, filed Oct. 31, 2005, now U.S. Pat. No. 7,687,037; and said 12/623,007, filed Nov. 20, 2009, is a continuation of U.S. patent application Ser. No. 11/264,670, filed Oct. 31, 2005, now U.S. Pat. No. 7,687,037; all of which are herein incorporated by reference.

This is a continuation-in-part of U.S. patent application Ser. No. 13/009,574, filed Jan. 19, 2011; which is a continuation of U.S. patent application Ser. No. 12/623,007, filed Nov. 20, 2009; which is a continuation of U.S. patent application Ser. No. 11/264,670, filed Oct. 31, 2005, now U.S. Pat. No. 7,687,037; and said 12/623,007, filed Nov. 20, 2009, is a continuation of U.S. patent application Ser. No. 12/243,635, filed Oct. 1, 2008, now U.S. Pat. No. 7,687,038; which is a continuation-in-part of U.S. patent application Ser. No. 11/264,670, filed Oct. 31, 2005, now U.S. Pat. No. 7,687,037; all of which are herein incorporated by reference.

BACKGROUND

1. Field of the Invention

The present invention relates generally to air fresheners.

2. Related Art

Air fresheners are common devices used to improve and/or change the olfactory characteristics of an environment. Such environments can include bathrooms or wash closets, vehicles, lockers, drawers, etc. Such air fresheners typically include a scent that is aesthetically pleasing, such as flowers, fruits, etc.

One common type of air freshener is a two-dimensional, paper-fiber card with a fragrance surrounded in a clear plastic envelope. The envelope is pierced to form an opening, and a portion of the freshener protrudes through the opening to release a scent. The air freshener includes a string or elastic forming a loop to suspend the air freshener. Such air fresheners are commonly utilized in vehicles. One disadvantage with such air fresheners is that the card is moist, and can leak or leach, leaving a stain on other surfaces, such as dashboards. The plastic envelope and the suspending loop act to resist contact between the card, and other surfaces. Another disadvantage with such air fresheners is that they are aesthetically displeasing. Another disadvantage with such air fresheners is that they have a more pronounced and immediate scent release, releasing a majority of the scent in the first few days of use.

Another common type of air freshener has a disc-shaped shell or canister with a scented disc or gel inside. The shell can include an adhesive strip to stick or adhere the shell to a surface. One disadvantage with such air fresheners is that removal of the shell often leaves a residue of the adhesive on the surface, which is aesthetically displeasing. In addition, the scented material can leak and harm the surface.

Some disadvantages of common air fresheners include 1) rapid scent loss or lack of longevity; 2) non-linear or inconsistent scent release over time; and 3) risk of staining. Some air fresheners disperse their scent too rapidly, thus losing effectiveness over time, and not lasting as long as desired. Some air fresheners quickly or rapidly disperse their scent after activation, and then slowly release scent, or release little scent, thereafter. Some air fresheners include materials that can leak and stain.

Another disadvantage with some air fresheners is that they include a non-solid and non-liquid material, or a jelly-like material, that must be contained in some type of container because the jelly is flowable. The material can become dried and cracked over time, presenting an aesthetically displeasing appearance. Again, the scented material can leak and damage surfaces.

SUMMARY OF THE INVENTION

It has been recognized that it would be advantageous to develop an air freshener that is more aesthetically pleasing. In addition, it has been recognized that it would be advantageous to develop an air freshener that is easily located or positioned without marring or otherwise damaging other surfaces. In addition, it has been recognized that it would be advantageous to develop an air freshener with a pivoting head configured to engage an air vent.

The invention provides an air freshener with at least one vent rod configured to engage an air vent. A scent material is associated with the at least one vent rod. A head is pivotally coupled to the at least one vent rod. A hinge is between the head and the at least one vent rod including a clip engaged in an aperture. One or more ridges correspond to one or more depressions associated with the clip and the aperture. The clip compresses as a ridge is forced out of a depression when the head is pivoted with respect to the at least one vent rod. The one or more ridges and the one or more depressions define various different positions of the head with respect to the at least one vent rod In addition, the invention provides an air freshener with a rod and a scent material carried by the rod. A head is pivotally coupled to the rod. A hinge is between the head and the rod including an axel in an aperture. A plurality of petals is coupled to the head and pivotal with the head with respect to the rod.

Furthermore, the invention provides an air freshener with a vent rod configured to engage an air vent. The vent rod has a length configured to extend into the air vent, and a width that varies along the length and that is less than the length. A polymer body is carried by the vent rod and has a scent material therein. A head is pivotally coupled to the vent rod. A hinge is between the head and the vent rod and includes a clip in an aperture. One or more ridges correspond to one or more depressions associated with the clip and the aperture. The clip compresses as a ridge is forced out of a depression when the head is pivoted with respect to the at least one vent rod. The one or more ridges and the one or more depressions define various different positions of the head with respect to the vent rod. A plurality of petals is coupled to the head and pivotal with the head with respect to vent rod. A bore is in the head, with the plurality of petals coupled to the bore. A ferrule has an open end receiving a portion of the plurality of petals, and an opposite end received within the bore of the head. A hook extends from the rod and around a portion of a pivot axis of the hinge, and has a free end extending in substantially the same direction as the rod.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIG. 1b is a bottom view of the air freshener of FIG. 1a;

FIG. 1c is a side view of the air freshener of FIG. 1a;

FIG. 1d is an opposite side view of the air freshener of FIG. 1a;

FIG. 3b is a side view of the rod of FIG. 3a;

FIG. 3c is an opposite side view of the rod of FIG. 3a;

FIG. 3d is a bottom view of the rod of FIG. 3a;

FIG. 3e is a top view of the rod of FIG. 3a;

FIG. 3f is a partial detailed perspective view of the rod of FIG. 3a;

FIG. 4a is a perspective view of the head of the air freshener of FIG. 1a shown with the petals and the rod removed;

FIG. 4b is a side view of the head of FIG. 4a;

FIG. 4c is an end view of the head of FIG. 4a; and

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Definitions

The term "scent material" and "fragrant material" are used interchangeably herein to refer broadly to a material that carries a desired fragrance or scent that can be discernable or smelled, or even a neutralizing agent. Thus, the scent or fragrance can be an ascertainable smell used to cover other scents, or a neutral agent that eliminates odors or provides a fresher atmosphere.

Description

Figure 1A:
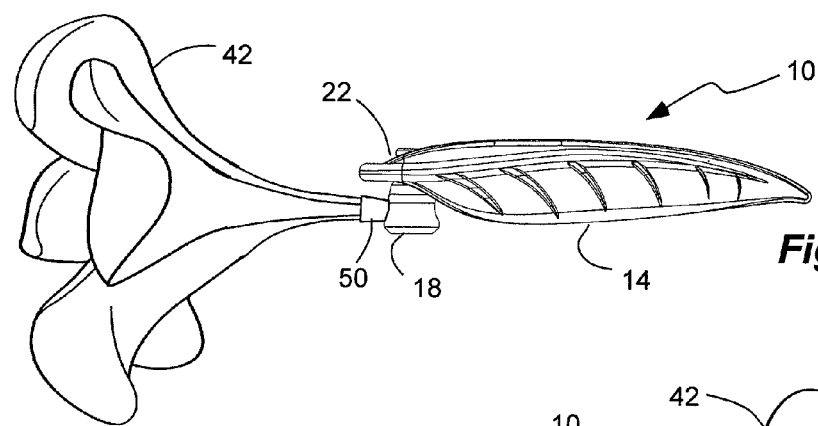
FIG. 1a is a top view of an air freshener device in accordance with an aspect of the present invention shown with a head thereof facing outwardly along a longitudinal axis of the device or rod thereof.
Figure 1B:
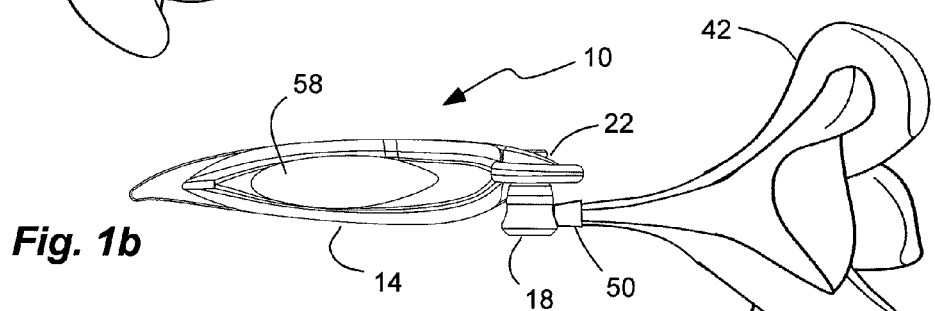
Figure 1C:
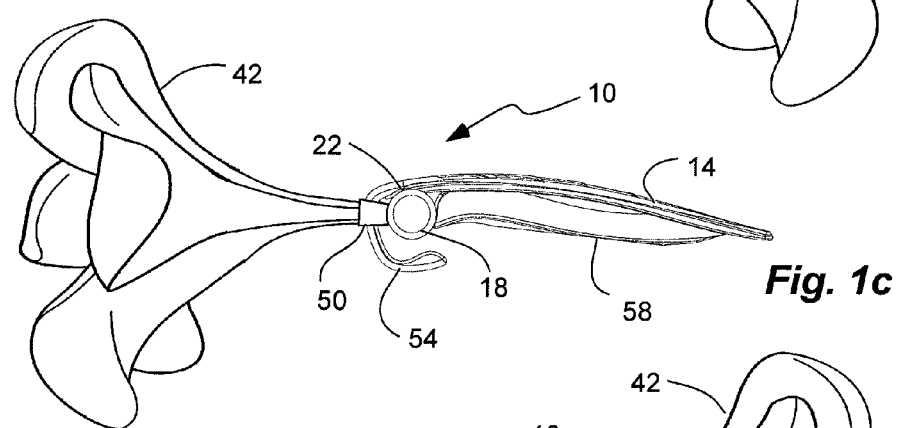
Figure 1D:
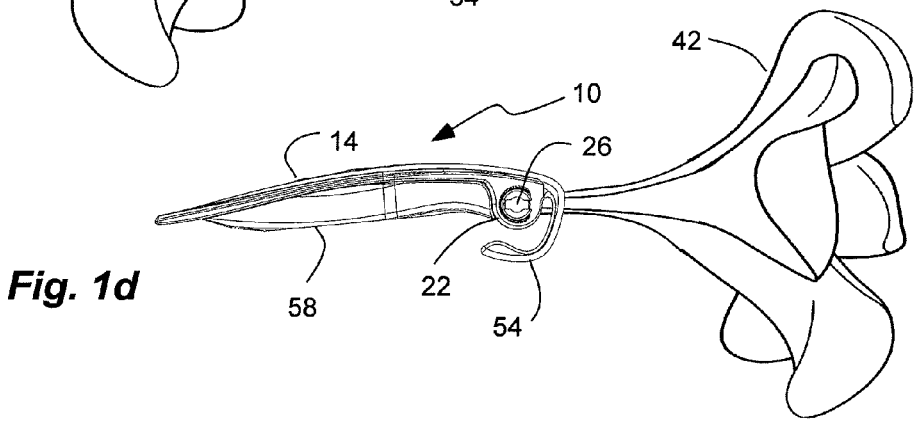
Figure 1E:
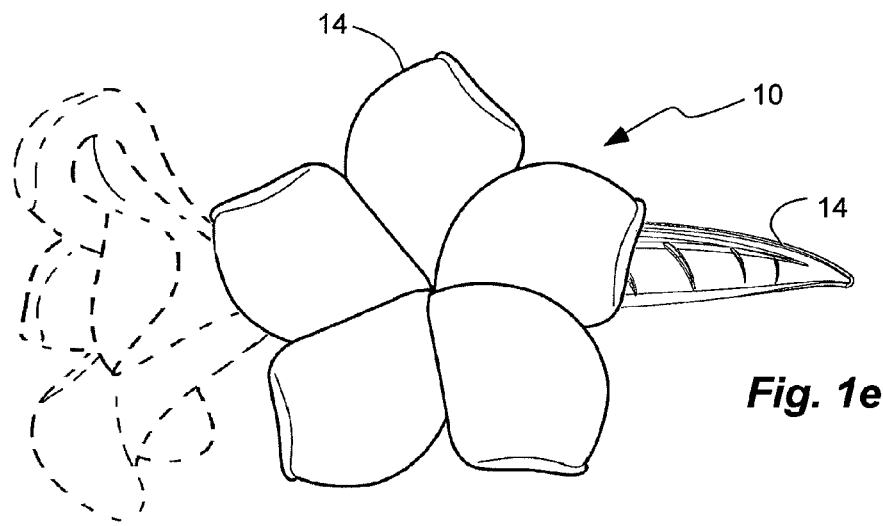
FIG. 1e is a top view of the air freshener of FIG. 1a shown with the head facing perpendicular to the longitudinal axis.
Figure 1F:
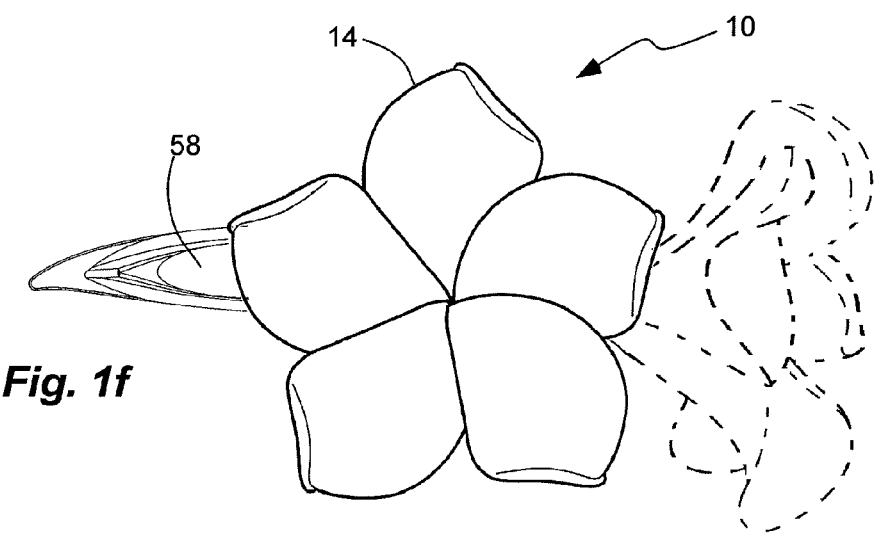
FIG. 1f is a bottom view of the air freshener of FIG. 1a shown with the head facing perpendicular to the longitudinal axis in an opposite direction with respect to FIG. 1e.
Figure 1G:
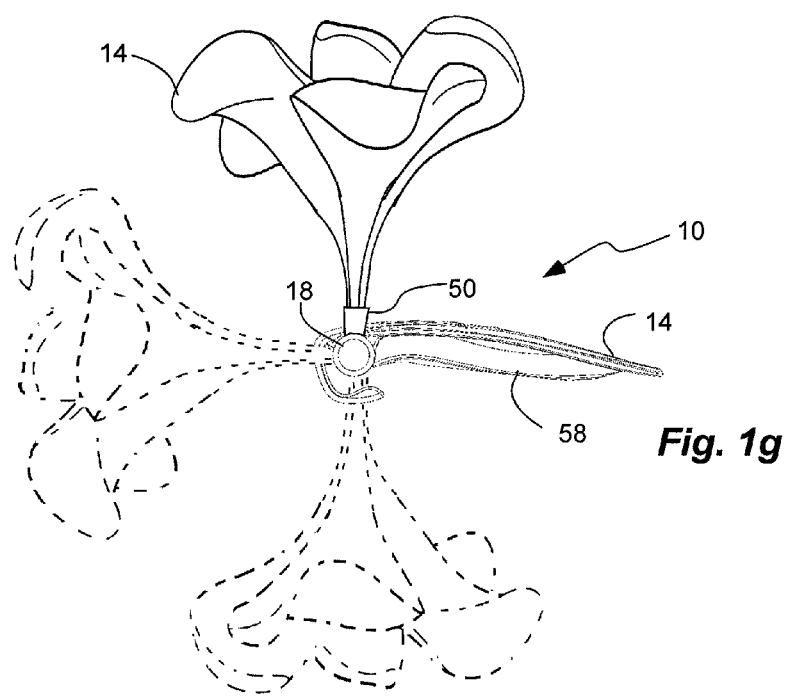
FIG. 1g is a side view of the air freshener of FIG. 1a shown with the head facing perpendicular to the longitudinal axis.
Figure 1H:
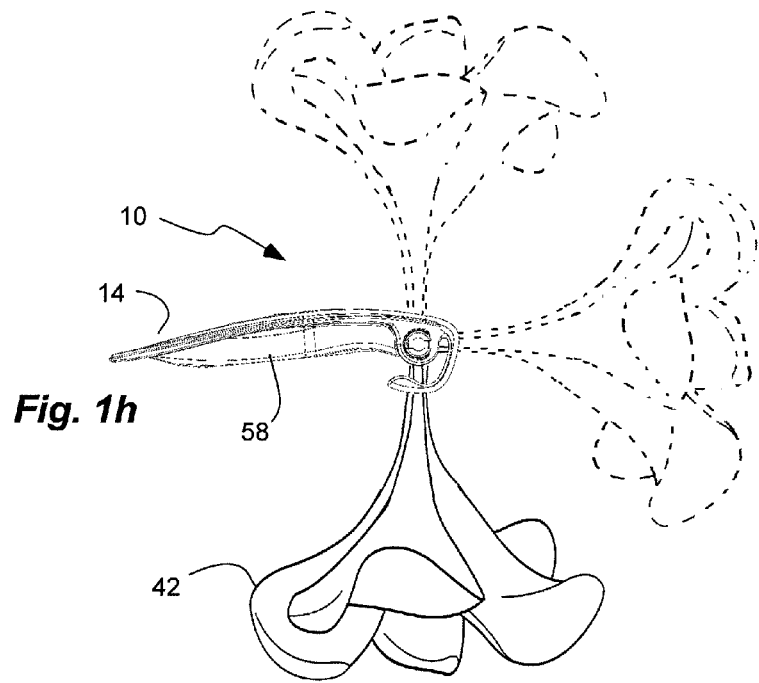
FIG. 1h is an opposite side view of the air freshener of FIG. 1a shown with the head facing perpendicular to the longitudinal axis in an opposite direction with respect to FIG. 1g; with FIGS. 1a-h showing the pivotal range of the head with respect to the rod.
Figure 2A:
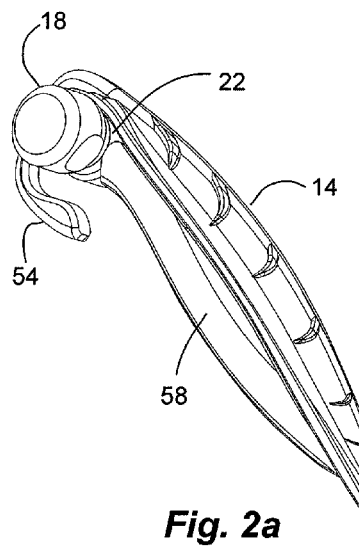
FIGS. 2a-d are perspective views of the air freshener device of FIG. 1a shown with petals of the head removed.
Figure 2B:
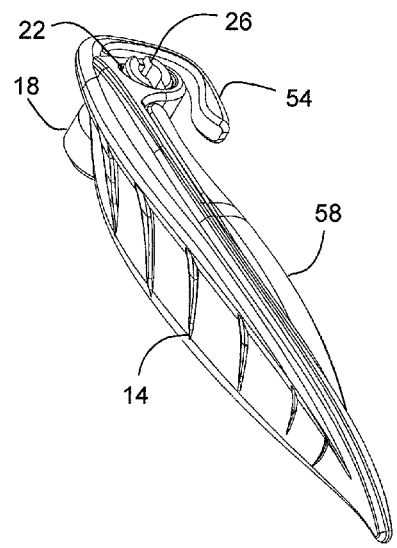
Figure 2C:
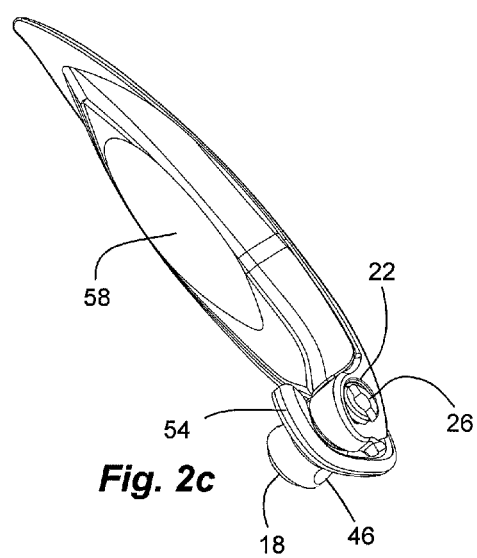
Figure 2D:
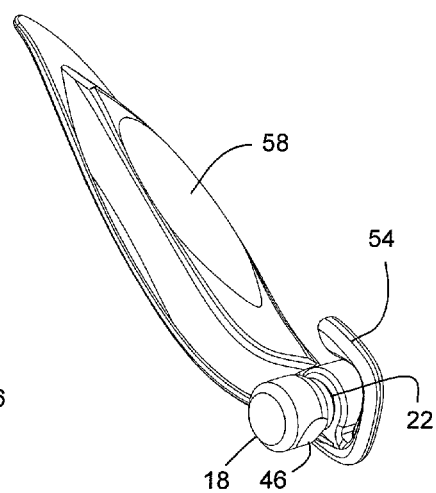
Figure 3A:
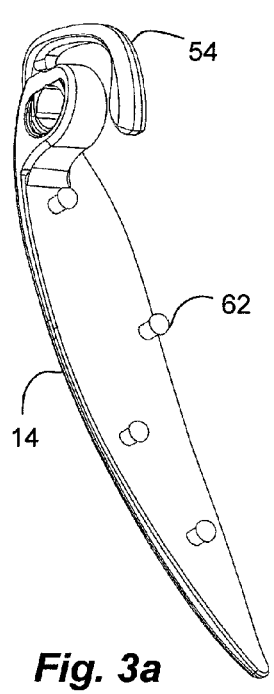
FIG. 3a is a perspective view of the rod of the air freshener of FIG. 1a shown with the head and a polymer body removed.
Figure 3B:
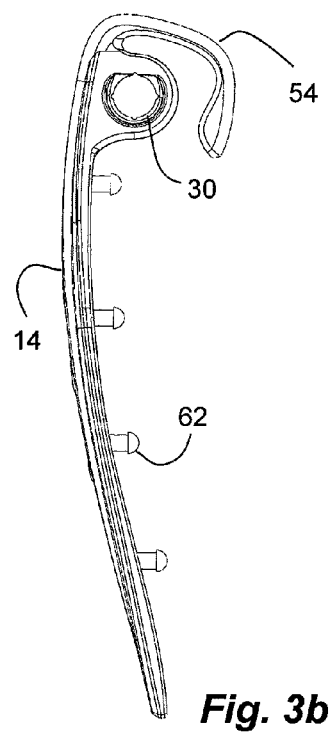
Figure 3C:
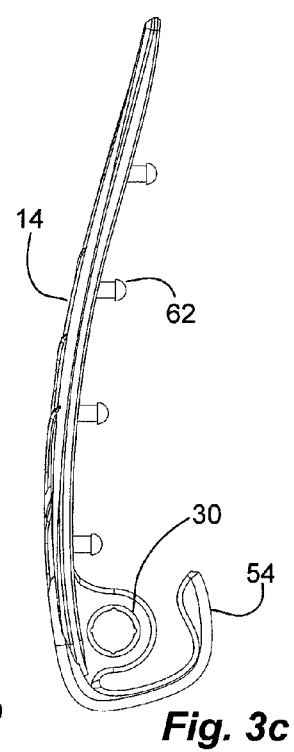
Figure 3D:
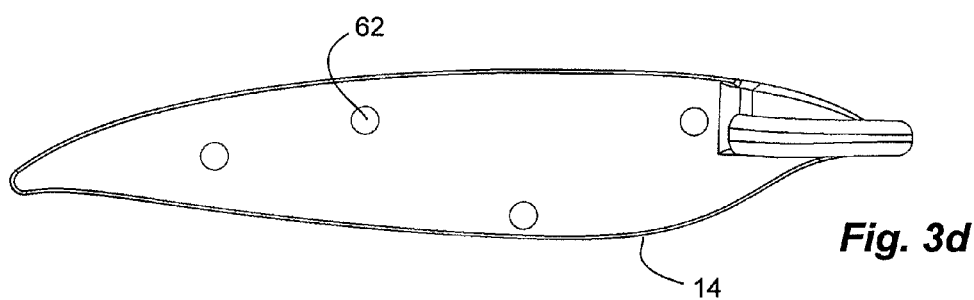
Figure 3E:
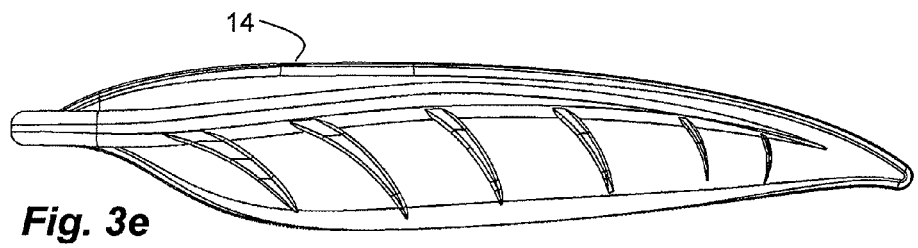
Figure 5:
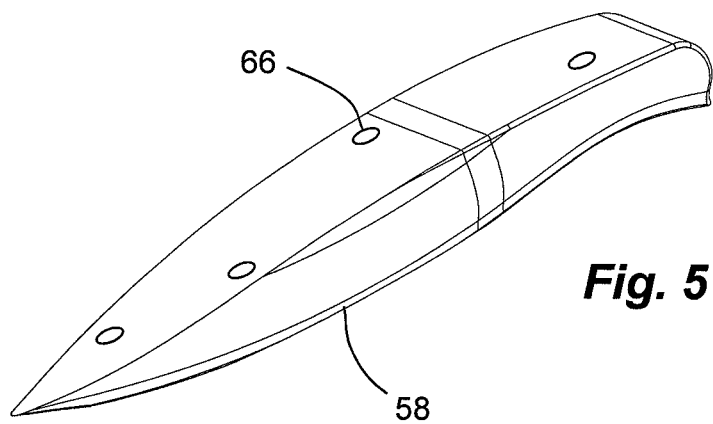
FIG. 5 is a perspective view of the polymer body of the air freshener of FIG. 1a shown removed from the rod.

As illustrated in FIGS. 1a-5, an air freshener or scent device, indicated generally at 10, in accordance with the present invention is shown for providing a desired and/or aesthetically pleasing scent, fragrance, aroma or neutralizing agent. Air fresheners are one example of a field that can benefit from the present invention. The air freshener 10 can be used in bathrooms, wash closets, vehicles, offices, bedrooms, etc. The desired scent can include, for example, floral, fruit, vanilla, berry, pine, etc. The air freshener can have a head that pivots with respect to a body. For example, the head and/or air freshener can be configured as a flower or portion thereof with petals that pivots with respect to the body. The body can also be configured as a flower or portion thereof, such as a leaf, and can be configured as a vent rod to extend into an air vent. Thus, the head and petals can pivot with respect to the body or rod between various different positions, such as a packaged configuration in packaging, and an in use configuration in an air vent, with the head and petals pivoted for display in both configurations.

The air freshener 10 can include one or more rods or vent rods 14 configured to engage an air vent, or the grid or louvers thereof. The vent rod can have a length configured to extend into the air vent or duct. The vent rod can be non-linear, and can have a curvilinear length. In addition, the vent rod can have a width less than the length, and that varies along the length. Thus, the rod can be sized and shaped as a leaf with a broad curvature including an outer convex surface with protrusions and/or indicia to appear as a leaf, such as veins, and an inner concave surface to receive a carries material, as discussed in greater detail below. In addition, the rod can widen and narrow from a proximal to a distal end, with a wider intermediate portion. The rod can have or can define a longitudinal axis oriented along the length or long dimension thereof so that the longitudinal axis extends into and from the air vent. The rod can be formed of plastic, and can be substantially or relatively rigid. A scent material with a desired scent or fragrance can be associated with and carried by the vent rod, as discussed in greater detail below.

The air freshener 10 can also include a head 18 pivotally coupled to the vent rod 14. A hinge 22 can be formed or defined between the head and the vent rod to allow the head to pivot with respect to the vent rod. The head and the vent rod can have multiple configurations with respect to one another, such as: a storage or packaged configuration (FIGS. 1e and 1g, or 1f and 1h) with a face of the head substantially facing a direction perpendicular to the longitudinal axis of the vent rod, and an in use configuration (FIGS. 1a-d) with the face of the head facing in a direction substantially parallel to the longitudinal axis of the vent rod.

The hinge 22 can include a clip or axel 26 engaged in an aperture 30. For example, the clip or axel 26 can be formed on the head 18, and the aperture 30 can be formed in the proximal end of the rod 14. The clip or axel can extend from the head and can be barrel-shaped or cylindrical, and bifurcated to form to halves or arms of the clip with a slot therebetween to allow the arms of the clip to resiliently and elastically bend or flex towards one another. The clip or arms thereof can have an outer diameter matching the inner diameter of the aperture. In addition, a flange 32, or flange halves, can be formed on distal ends of the clip or arms thereof. The flange can have an outer diameter greater than the inner diameter of the aperture to retain the clip or axel in the aperture. Furthermore, the arms, clip or axel can be longer than the aperture so that the flange is disposed outside of the aperture. The aperture 30 can extend through the proximal end of the rod. The aperture 30 can be formed an annular portion extending from the rod with the annular portion extending towards the concave portion and away from the longitudinal axis, and the aperture oriented transverse to the longitudinal axis and along the width of the rod. The ends of the clip or axel can be pressed together, aided by an inclined leading edge of the flanges of the arms, to insert the arms of the clip into and through the aperture. As the flanges clear the aperture, the resiliency and elasticity of the arms returns the arms to a parallel initial configuration with the flanges extending beyond the aperture both longitudinally and radially retain the clip in the aperture. A portion of the head opposite the flanges can also be enlarged with respect to the clip or axel to retain the aperture or annular portion of the rod between the flange and enlarged portion of the body. Thus, the enlarged portion and flange form a hub with an annular groove. In one aspect, the head can be removably coupled to the vent rod by pressing the arms of the clip together and withdrawing the clip from the aperture. One advantage of a removable head is that it allows a user to replace a vent rod or a polymer body after the scent has fully vented from the device, or to exchange it for a vent rod or a polymer body having a different desired scent, or the exchange different heads with respect to the rod or body.

In addition, the hinge can include one or more ridges 34 corresponding to one or more depressions 38 associated with the clip and the aperture to set or bias the orientation of the head with respect to the rod, and allowing the orientation to be changed. For example, the ridges 34 can be formed in the clip or axel 26, while the depressions 38 can be formed in the aperture. When the head and clip are rotated in the aperture, the clip compresses and the arms come together as a ridge is forced out of a depression. The one or more ridges and the one or more depressions define various different positions of the head with respect to the vent rod. When the head is pivoted to a different position, the ridge can enter a different depression and engage into the different position. The clip or axel rotating or pivoting in the aperture can define a pivot axis. The head and clip or axel can be formed of plastic.

The head 18 and the air freshener 10 can include a plurality of petals 42 coupled to the head and pivotal with the head with respect to the vent rod. The petals or a proximal end thereof can be coupled to a bore 46 in the head. The bore can extend through the head and can be oriented transverse to the clip or axel, the aperture, and pivot axis thereof. In addition, a ferrule 50 can be used to couple the petals to the head. The ferrule can include an open end receiving a portion or proximal ends of the plurality of petals, and an opposite end received within the bore of the head. The petals can be adhered to the ferrule, and the ferrule can be adhered to the bore of the head. The petals can be formed of or can include polyurethane. Alternatively, the petals can be formed of urethane or foam. The petals can be colored. The ferrule can be tubular with a segmented end to receive the petals. The ferrule can be formed of plastic.

The petals can form a portion of the head or can be a part of the head. In addition, the petals can form a face of the head. The face can face along an axis of the bore in the head, transverse to the pivot axis and axis of the aperture. As described above, the head and face can be pivoted with respect to the vent rod. Thus, the face can be oriented between different orientations for packaging and in use in an air vent. The air freshener 10 can be provided in a packaging system for presenting the air freshener for purchase. The packaging can include a blister pack and/or clam shell packaging that is transparent with a planar card therein, and with one or more air fresheners contained therein. The package can provide a container for containing the air freshener device. The container or package can be configured to display a face of the head in a position to substantially face outwardly, perpendicularly to the longitudinal axis of the vent rod. The vent rod can be parallel with the card, and the head can be pivoted to face outwardly along with the card to display the head. When remove from packaging, the head can be capable of pivoting to a different position for use where the face can face along the longitudinal axis of the vent rod. Thus, the head and/or petals can be readily visible in both packaging and use configurations.

The air freshener 10 or vent rod 14 can also include a hook 54 that can extend from the rod, or proximal end thereof, and around a portion of the pivot axis of the axel in a spaced-apart relationship to the rod, and with a gap or slot therebetween. The hook 54 can be arcuate and can extend to a free end extending in substantially the same direction as the rod. The hook and the rod can work together to engage an air vent or louver thereof. Alternatively, the hook can be used to affix or couple the air freshener to another object.

As described above, the scent material can be carried by the vent rod. In addition, the scent material can be in a polymer body or carrier material 58 carried by the vent rod. The carrier material or polymer body can have a size and shape similar to the size and shape of the rod. Thus, the polymer body can be non-linear and can have a length longer than a width, and a width and thickness, or cross-sectional shape, that varies along the length. The polymer body can have an exposed side or surface with indicia thereon. The carrier material or polymer body can be coupled to the rod and extend into the air vent with the rod. In one aspect, the rod can have a plurality of protrusions 62 spaced at predetermined intervals along the rod, and the carrier material or polymer body can have a plurality of apertures 66 corresponding to the protrusions on the rod. The carrier material or polymer body can be coupled to the rod by snapping the apertures onto the protrusions. In this way, the carrier material or polymer body can be inserted with the rod into the air vent to increase scent dispersal as air blows through the vent and through or around the polymer body. The rod and polymer body together can define a body of the air freshener with respect to the head thereof.

The polymer body can be flexible and resilient, such as a polymer gel. The polymer body can be elastic and coherent. Thus, the polymer body can be compressible under an applied force, and substantially returnable to an original configuration upon removal of the applied force. It has been found that the polymer gel provides desired characteristics of aesthetics, flexibility, longevity, substantially constant scent release, and containment. In accordance with another aspect of the present invention, the polymer gel can have a freestanding, self-supported, three-dimensional shape that does not significantly change as the scent is released. The carrier material or polymer body can have a scent material of the desired scent interspersed therein. The scent material disperses or diffuses out of the carrier material or polymer body into the air or atmosphere where it can be detected, or where it can provide a discernable scent. It is believed that the scent material migrates or diffuses through and out of the carrier material or polymer body. The scent material can be high in volatile notes, or has high volatility and can vaporize or evaporate at low temperatures. The scent material can include a scented oil. For example, suitable scent material can include pine, berry, vanilla, apple, coconut, cherry, pina colada, etc.

The carrier material or polymer body can include a polymer material, such as a polymer gel. The polymer body and/or polymer gel can be elastic and coherent. Thus, the polymer body can elastically deform under normal conditions. The polymer body can be flexible and resilient, such that the body or gel can compress under an applied force, but can substantially return to its original configuration upon removal of the applied force. The polymer gel, or the polymer body, can have a freestanding, self-supported, three-dimensional shape. Thus, the polymer gel or polymer body can be consistent or solid enough to support or maintain its shape in a freestanding manner without a container. The three-dimensional shape can be any desired shape. The polymer gel can be considered a solid material that is elastic and coherent, and thus flexible and capable of being deformed, but without being flowable.

Thus, the polymer gel may have a sufficiently high molecular weight, and/or a sufficiently high viscosity, so that it is a non-flowable gel. In addition, the polymer gel can be considered as stable. Thus, the polymer gel can be bendable, but otherwise substantially maintains its form. The polymer body or polymer gel can be characterized as a polymeric material in the glass state with substantially no macroscopic flow. The polymeric material can have a glass transition temperature greater than approximately 110° F. The polymer gel can retain its gel-like characteristic over time, without drying or cracking, and without becoming hard or brittle.

In one embodiment, the polymer gel or polymer body can include a polyurethane material or can be a polyurethane gel. The gel can be formed by combining a polyurethane material with a scented oil. Surprisingly, it has been found that such a combination provides a desired scent, but without staining or substantially leaking onto a surface. In addition, the polymer body does not undergo a visually ascertainable physical change, such as drying out or cracking. Thus, the polymer body remains aesthetically pleasing.

In some embodiments, a scented oil and a polymerizable monomer can be combined, along with optional initators or other reactants. Isocyanate reaction polymers have shown good results in connection with the present invention. For example, the polymer gel and scent material can be a urethane polymerization product of combining a scented oil with a polyether polyol, and then with a diphenylmethane diisocyanate (MDI) prepolymer. Therefore, in some embodiments, the scent material can be a scented oil which participates in the polymerization reaction between polymerization reactants. For example, essential oils such as terpenes and the like can be mixed with polymerization reactants, or even in place of some reactants. Without being bound by any particular theory, it is thought that at least some of the reduction or elimination in residue in the devices of the present invention result from at least partial replacement of mineral oils and/or polyols with scented oils such as those listed herein. Other suitable isocyanates can include, but are not limited to, tolylene diisocyanates, methylene diphenyl isocyanates, hexamethylene diisocyanates, prepolymers thereof, and the like. Those skilled in the art will recognize various other isocyanate reaction polymers, i.e. polyurethanes, which can be suitable for use in connection with the present invention.

Alternatively, the polymer gel or polymer body can include silicone, diffused polyurethane, polyvinylchloride (PVC), ethylene vinyl acetate (EVA), thermoplastic polyurethane (TPU), a polymer encapsulation fragrance delivery platform (PolyIFF®), thermoplastic elastomer (TPE), polypropylene, ethylene/methacrylic acid (E/MAA) copolymer, in which the MAA groups have been partially neutralized with lithium ions (Surlyn® Dupont), etc.

As a general guideline, the polymer gel or polymer body can be formed of an elastomer such as, but not limited to, urethanes (including polyester and polyether polyol/isocyanate polymerization products), polyacrylates, polybutadienes, ethylene propylene elastomers, silicones, natural and synthetic rubbers, styrene/butadiene block copolymers, and the like. In some embodiments, the polymer gel can be formed of a thermoplastic elastomer. Thermoplastic elastomers can be block copolymers such as polyurethanes, polyamides, copolyesters, and styrene-butadiene-styrene polymers. Other thermoplastic elastomers can be elastomer/thermoplastic blends such as ethylene-propylene-diene monomer in an isotactic polypropylene phase or nitrile rubber dispersed in a PVC phase. As used herein, "thermoplastic elastomer" refers to an elastomer which can be heated and processed like thermoplastic materials. Specifically, a thermoplastic elastomer can be heated to a melted or flowable state and then cooled, resulting in reformation of cross-linking and subsequent coherency without a substantial change in mechanical properties such as strength, flexural modulus, elastic modulus, etc.

As used herein, "elastomeric polymer" and "elastomer" may be used interchangeably and refer to a polymeric material which can be mechanically deformed and upon release returns to an original shape. A coherent elastomer is also non-flowable at or near room temperatures. Further, "cling" and "clingy" refer to a property of a polymeric material which imparts adhesion to most surfaces without a loss of coherency in the polymer. Typically, removal of an elastomeric polymer body with a clingy attachment surface from a substrate does not result in substantial deformation, including temporary deformation, during flexing of the elastomer and/or attachment surface. A clingy attachment surface can be provided directly by the polymer body or can be provided in a separate layer as discussed in more detail herein. Adhesion can occur via mechanical adhesion or specific adhesion. Specific adhesion refers to adhesion dominated, or entirely characterized, by secondary intermolecular forces, i.e. non-covalent bonds, although some covalent bonds can be formed.

Although the polymer gel or polymer body is freestanding and self-supporting, it is also flexible and resilient. Thus, polymer body or carrier material can form a flexible and resilient structure or body that can be selectively deformed and can return substantially to the three-dimensional shape. In addition, the carrier material or polymer body can be opaque. Alternatively, the carrier material or polymer body can be light transmissive in at least a translucent manner.

The air freshener device can be shaped, sized and/or colored to appear as another object that can be complimentary to the provided scent or fragrance. For example, the desired scent or fragrance can be floral, and the air freshener can be configured as a flower or portion thereof. The petals and head can be configured as a head of a flower. The rod and the polymer body can be configured as a leaf or petal. The rod and polymer body can have a curvilinear, variable cross-section, organic shape. A top of the rod, opposite the polymer body can have protrusions forming veins of a leaf.

It is contemplated that other materials or configurations may be also used to pivot the head with respect to the vent rod, such as joint configurations known in the art or bendable wire, rubber, or plastic materials and the like.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. An air freshener device, comprising:
   a) a rod;
   b) a scent material carried by the rod;
   c) a head pivotally coupled to the rod;
   d) a hinge between the head and the rod including an axel in an aperture; and
   e) a plurality of petals coupled to the head and pivotal with the head with respect to the rod.

2. The device in accordance with claim 1, further comprising:
   a bore in the head, with the plurality of petals coupled to the bore.

3. The device in accordance with claim 2, further comprising:
   a ferrule with an open end receiving a portion of the plurality of petals, and an opposite end received within the bore of the head.

4. The device in accordance with claim 1, further comprising:
   a polymer body carried by the rod and having the scent material therein.

5. The device in accordance with claim 1, wherein the hinge further comprises:
   one or more ridges corresponding to one or more depressions associated with the axel and the aperture, the axel compressing as a ridge is forced out of a depression when the head is pivoted with respect to the rod, the one or more ridges and the one or more depressions defining various different positions of the head with respect to the rod.

6. The device in accordance with claim 1, wherein the rod has a width greater than a thickness, and a length greater than the width.

7. The device in accordance with claim 1, wherein the rod is non-linear.

8. The device in accordance with claim 1, wherein the rod has a variable width along a length thereof.

9. The device in accordance with claim 1, further comprising:
   a hook extending from the rod and around a portion of a pivot axis of the axel, and having a free end extending in substantially the same direction as the rod.

10. An air freshener device, comprising:
   a) at least one vent rod configured to engage an air vent;
   b) a scent material associated with the at least one vent rod;
   c) a head pivotally coupled to the at least one vent rod;
   d) a hinge between the head and the at least one vent rod including a clip engaged in an aperture; and
   e) one or more ridges corresponding to one or more depressions associated with the clip and the aperture, the clip compressing as a ridge is forced out of a depression when the head is pivoted with respect to the at least one vent rod, the one or more ridges and the one or more depressions defining various different positions of the head with respect to the at least one vent rod.

11. The device in accordance with claim 10, further comprising:
   a plurality of petals coupled to the head and pivotal with the head with respect to the at least one vent rod.

12. The device in accordance with claim 11, further comprising:
   a bore in the head, with the plurality of petals coupled to the bore.

13. The device in accordance with claim 12, further comprising:
   a ferrule with an open end receiving a portion of the plurality of petals, and an opposite end received within the bore of the head.

14. The device in accordance with claim 10, further comprising:
   a polymer body carried by the at least one vent rod and having the scent material therein.

15. The device in accordance with claim 10, wherein the at least one vent rod has a width greater than a thickness, and a length greater than the width.

16. The device in accordance with claim 10, wherein the at least one vent rod is non-linear.

17. The device in accordance with claim 10, wherein the at least one vent rod has a variable width along a length thereof.

18. The device in accordance with claim 10, further comprising:
   a hook extending from the at least one vent rod and around a portion of a pivot axis of the hinge, and having a free end extending in substantially the same direction as the at least one vent rod.

19. An air freshener device, comprising:
   a) a vent rod configured to engage an air vent, the vent rod having a length configured to extend into the air vent, and a width that varies along the length and that is less than the length;
   b) a polymer body carried by the vent rod and having a scent material therein;
   c) a head pivotally coupled to the vent rod;
   d) a hinge between the head and the vent rod including a clip in an aperture;
   e) one or more ridges corresponding to one or more depressions associated with the clip and the aperture, the clip compressing as a ridge is forced out of a depression when the head is pivoted with respect to the at least one vent rod, the one or more ridges and the one or more depressions defining various different positions of the head with respect to the vent rod;
   f) a plurality of petals coupled to the head and pivotal with the head with respect to the vent rod;
   g) a bore in the head, with the plurality of petals coupled to the bore;
   h) a ferrule with an open end receiving a portion of the plurality of petals, and an opposite end received within the bore of the head; and
   i) a hook extending from the rod and around a portion of a pivot axis of the hinge, and having a free end extending in substantially the same direction as the rod.

20. The device in accordance with claim 19, wherein the vent rod is non-linear.

* * * * *